United States Patent [19]
Johnson

[11] Patent Number: 5,243,639
[45] Date of Patent: Sep. 7, 1993

[54] FLOATABLE PATIENT SUPPORT BOARD HAVING AN X-RAY CASSETTE HOLDER

[76] Inventor: H. Clayton Johnson, 101 Chaparral Dr., Madison, Ala. 35758

[21] Appl. No.: 747,282

[22] Filed: Aug. 19, 1991

[51] Int. Cl.$^5$ .............................................. G03B 42/02
[52] U.S. Cl. ................................... 378/180; 378/177; 378/208; 5/601; 5/628
[58] Field of Search ............... 378/180, 177, 208, 209; 5/601, 606, 607, 600, 608, 610, 611, 628, 620, 625, 81.1

[56] References Cited

U.S. PATENT DOCUMENTS

| | | | |
|---|---|---|---|
| 4,193,148 | 3/1980 | Rush | 378/177 |
| 4,651,364 | 3/1987 | Hayton et al. | 378/177 |
| 4,736,474 | 4/1988 | Moran et al. | 5/628 |
| 4,893,323 | 1/1990 | Cook | 378/208 |
| 4,995,067 | 2/1991 | Royster et al. | 378/177 |
| 5,016,268 | 5/1991 | Lotman | 378/177 |

*Primary Examiner*—David P. Porta
*Assistant Examiner*—Kim-Kwok Chu
*Attorney, Agent, or Firm*—John C. Garvin, Jr.

[57] ABSTRACT

A combination spinal immobilization and x-ray examination board for use in extricating, rescuing and transporting a traumatized victim from the place of the trauma through hospital emergency room procedures including x-ray examinations. The board comprises a main patient support board having an x-ray cassette holder attached thereto which allows a trauma victim to be placed upon the board at the trauma scene, restrained thereto, and transported to an emergency room facility to undergo various procedures, tests and treatments including the taking of x-rays, without having to lift the patient from the board until after learning of the extent of the injuries suffered by the patient.

12 Claims, 4 Drawing Sheets

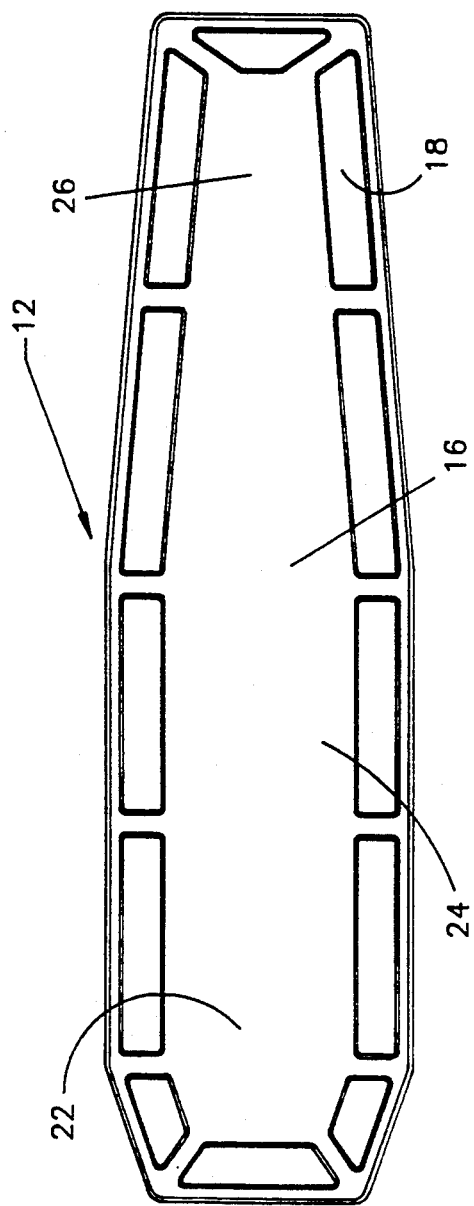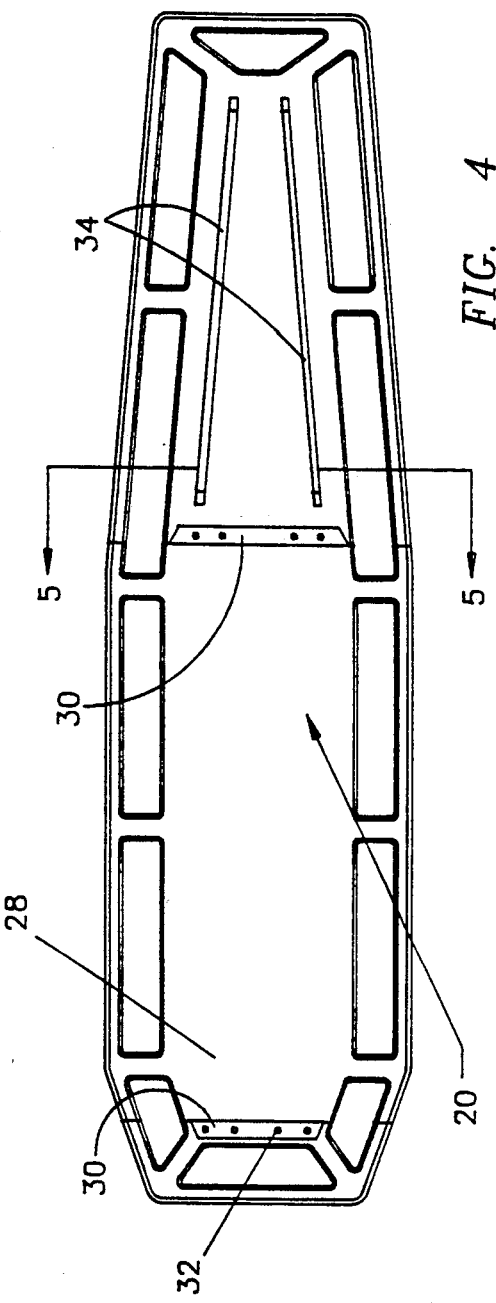

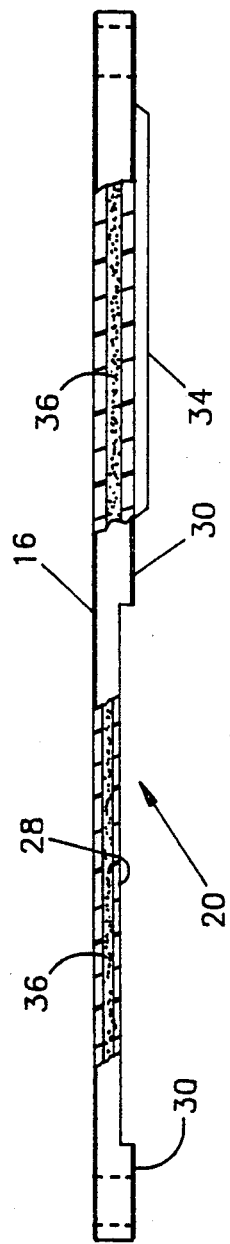
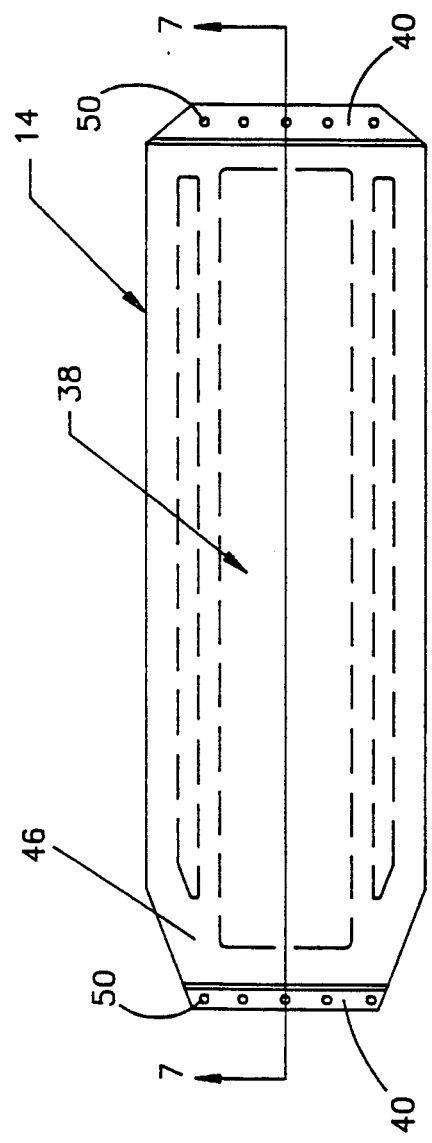
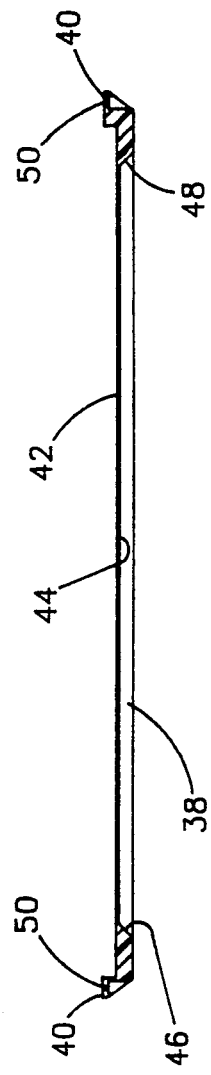

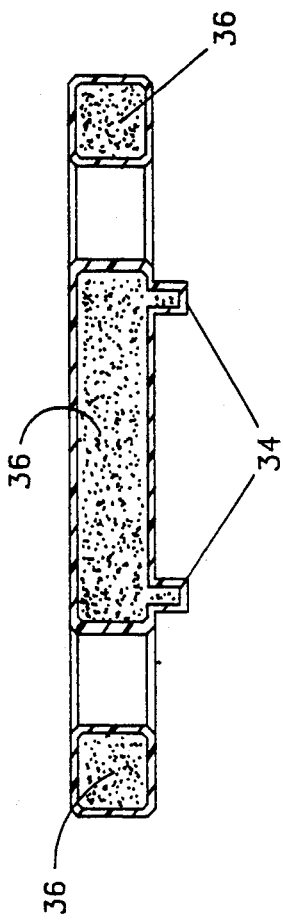
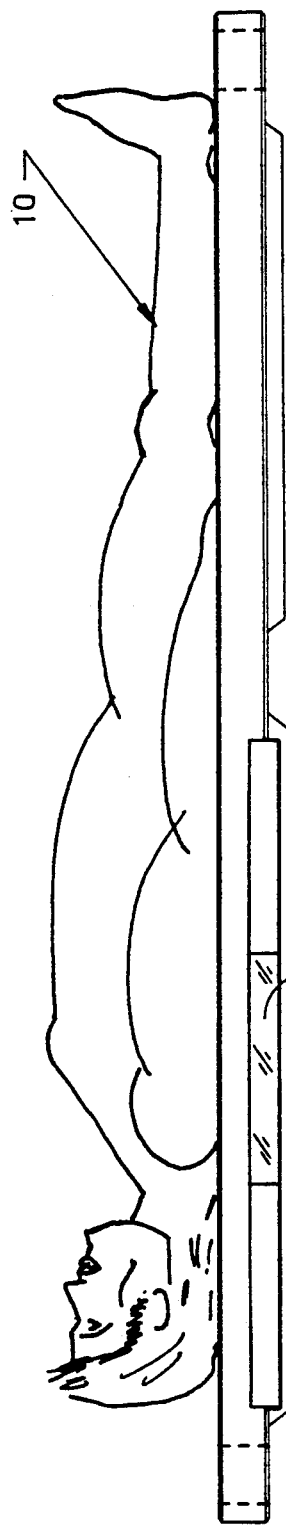
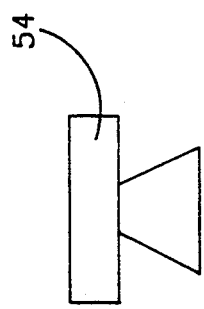

FLOATABLE PATIENT SUPPORT BOARD HAVING AN X-RAY CASSETTE HOLDER

FIELD OF THE INVENTION

The present invention relates generally to a patient handling apparatus and more particularly to an emergency spinal immobilization board for use in extricating, rescuing and transporting a traumatized victim from the place where the trauma occurred through hospital emergency room procedures for diagnosis, test and treatment including x-ray examinations.

BACKGROUND OF THE INVENTION

A person who has been seriously injured in an accident or from a sudden illness is usually initially attended by paramedics or ambulance crews and transported on a conventional stretcher, mobile bed or spine boards to an emergency room facility where necessary medical treatment can be rendered. Upon arrival at the emergency room facility the patient is generally transferred from the stretcher or mobile bed to an emergency room examining table, then to an x-ray table, back again to the emergency room examining table, and then possibly to a regular hospital bed. This constant movement of the patient can aggravate an injury, such as a suspected spinal injury, and even possibly cause additional injuries. While the immobilization of a patient at the scene of the trauma is generally recognized as a desirable course of action, it should be recognized that the high mortality rate occurring in emergency room facilities can be attributed, at least in part, to the repeated transfer of the patient through various diagnostic procedures on several support structures in lieu of maintaining the patient in an immobilized condition throughout on a single support structure. It is desirable to essentially immobilize the patient from the time that the patient is first placed on the support structure until after x-rays are taken so that the injury will not be further aggravated.

In researching spine boards presently used in the industry, a great shortcoming in such boards was found after the patient arrives at the hospital emergency room. Upon the patient's arrival, it is most important that the severity of injuries, particularly suspected spinal injuries, be immediately assessed. Presently this is normally achieved by one of three methods, namely, the transportation of the patient directly to the radiology department of the hospital; the transportation of the patient to the emergency room x-ray room if the hospital is so equipped; or in most cases, the patient is physically lifted to place an x-ray cassette under the patient, and a portable x-ray machine is used to perform lateral and anterior-posterior spinal examinations. The latter or most common method appears to be favored in that it is quick and convenient, however such method places the patient at greater risk of being jostled, or worse, being dropped, and also places physical stress on attending nurses and radiologic technologists. Other problems associated with this preferred method include distorted images due to poor cassette placement, which can lead to undiagnosed radiographs and retakes which result in unnecessary radiation exposure to both the patient and emergency room personnel.

Various devices have been proposed and used for immobilizing and transporting trauma victims with a minimum of body movement. The most commonly used transport device is a simple flat board; however, many more complex transport devices can be and have been used. Although these devices are adequate for transporting the patient from the trauma scene to the hospital emergency room, they create a problem when x-rays must be made of the patient since movement of the patient will be required to either transfer the patient from the transport device to the x-ray table or to insert an x-ray film under the patient while still on the transport device. Since many of these transport devices are made of material which contain artifacts or imperfections which might cause inaccurate x-ray readings, they should not be used in the taking of x-rays of the patient while being supported thereon.

Other problems associated with existing spine boards for rescuing trauma victims include splintering plywood which could prove to be dangerous, small runners, or no runners whatsoever, on the bottom of the board to allow for a firm grip during lifting, and an inadequate number of hand hold openings for grasping and for use in securing and adjusting straps for restraining the trauma victim upon the spine board. Many of the presently available spine boards are made of aluminum which hinders the incorporation of a floatation medium which is vital in the rescue of victims of water related accidents.

It is therefore desirable to provide an emergency spinal board for immobilizing and transporting a person from a trauma scene to an emergency room facility and which permits x-ray examination without further movement of the person from the spinal board and without interfering with the quality of the x-ray.

A search of the public records produced a limited number of combination stretchers and portable x-ray tables including U.S. Pat. Nos. 4,193,148; 4,651,364; 4,893,323; 4,926,457; and 4,947,418. None of these reference, either singly or in combination, show or suggest the present invention.

The present invention overcomes the numerous shortcomings and disadvantages of prior art devices and procedures by incorporating a cassette holder on the bottom side of the spine board which allows a radiologic technologist or other medical personnel to insert an x-ray cassette therein. The present invention further eliminates other problems associated with existing spine boards by providing a board of molded plastic construction which eliminates splintering and staining, by providing perimeter handles and slightly higher runners which raises the spine board and allows for grasping at any point along the spine board and linear adjustability of the restraining straps, and the provision of a floatation medium which makes the spine board buoyant which is critical in the rescue of water related accident victims.

SUMMARY OF THE INVENTION

The combination spinal immobilization and x-ray board of the present invention comprises a main or support board attached to an x-ray cassette holder which allows a trauma victim to be placed upon the board at the trauma scene, restrained thereto, transported to an emergency room facility, and undergo various tests and treatments, including the taking of x-rays, without having to lift the victim from the board until after learning of the extent of the injuries suffered by the victim.

An object of the present invention is to provide a patient handling apparatus for use in rescuing and transporting an injured or sick patient from a trauma scene to an emergency room facility, and which permits emergency room procedures without removing or lifting the patient from the apparatus.

Another object of the present invention is to provide a patient handling apparatus for use in rescuing and transporting an injured or sick patient from a remote site through emergency room diagnostic procedures, including the taking of x-rays, without lifting or removing the patient from the apparatus and possibly aggravating the injuries.

It is a further object of the invention to provide a patient handling apparatus that can be used in lieu of numerous other patient support structures by medical emergency personnel in rescuing, transporting, and diagnosing trauma victims, which is relatively simple in construction and economical to manufacture.

These objects as well as other objects of the present invention will become more readily apparent after reading the following description in conjunction with the accompanying drawings.

BRIEF DESCRIPTION OF THE DRAWINGS

FIG. 2 is a top plan view of the main or support board of the spinal immobilization board of the present invention.

FIG. 3 is a partially broken away side view of the main or support board of the spinal immobilization board of the present invention.

FIG. 4 is a bottom plan view of the main or support board of the spinal immobilization board of the present invention.

FIG. 5 is an enlarged cross sectional view of the main or support board of the spinal immobilization board of the present invention taken along line 5—5 of FIG. 4.

FIG. 6 is a top plan view of the x-ray cassette holder of the spinal immobilization board of the present invention.

FIG. 7 is a sectional view taken along line 7—7 of FIG. 6 of the x-ray cassette holder of the spinal immobilization board of the present invention.

FIG. 8 is a side view showing a patient lying on the immobilization board of the present invention and having his torso area being examined by an x-ray machine.

DESCRIPTION OF THE PREFERRED EMBODIMENT

Figure 1:
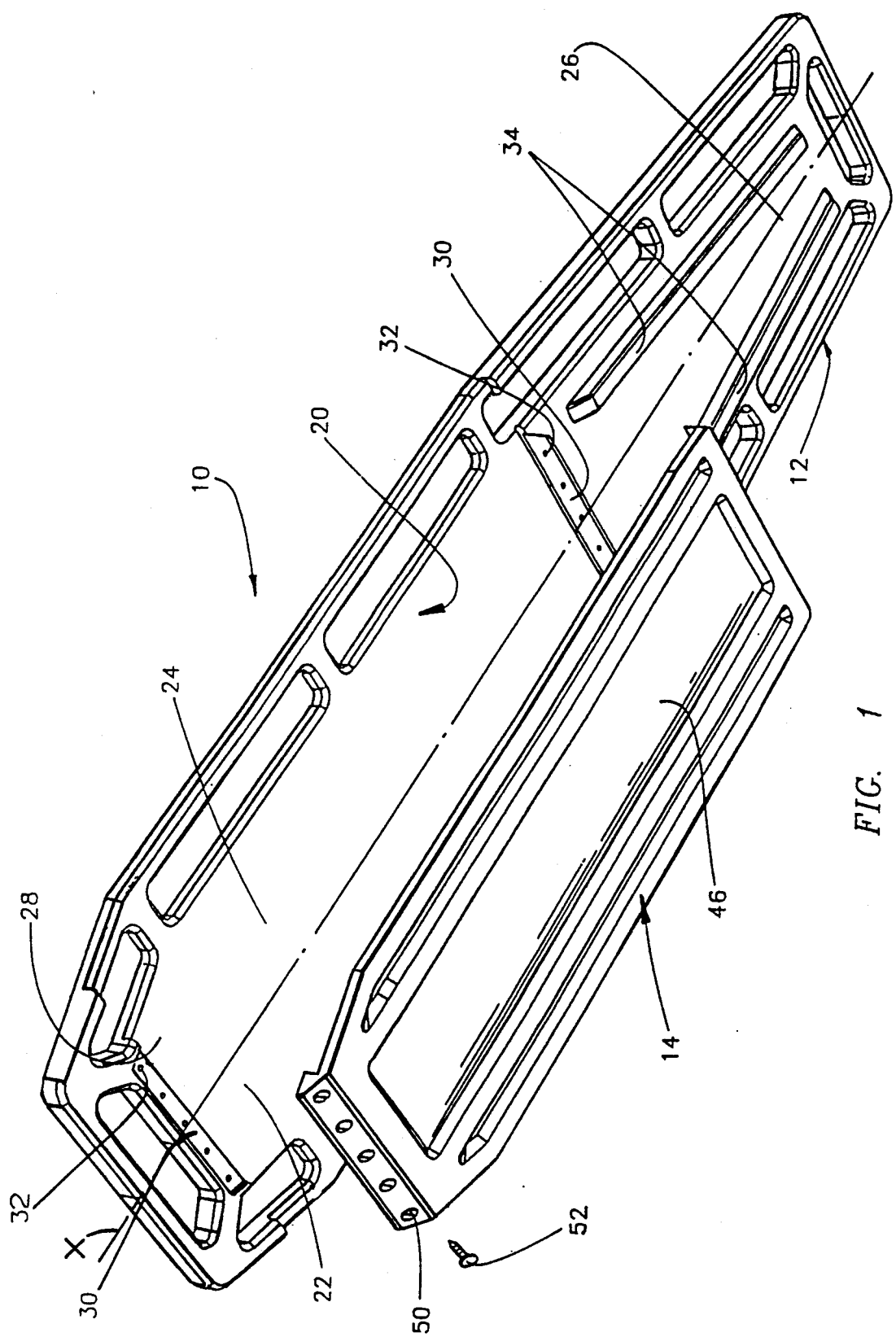
FIG. 1 is an exploded view of the spinal immobilization board of the present invention.

Referring now to FIG. 1 of the drawing, reference numeral 10 designates a medical apparatus which serves as both a spinal immobilization board for transporting a person to an emergency room facility and as a support structure for use in the taking of x-rays of such person. Medical apparatus 10 comprises a main or support board 12 and an x-ray cassette holder 14. Main board 12 is generally rectangular in shape, having a longitudinal axis X (FIG. 1) and comprises a top surface 16 (FIGS. 2 and 3), a plurality of openings or slots 18 therethrough and a bottom surface 20 (FIGS. 1 and 4). Main board 12 further includes an upper or head section 22 (FIG. 2), a mid or torso section 24, and a lower or leg section 26. The mid or torso section 24 of main board 12 is recessed on its bottom surface 20 as shown by reference numeral 28 (FIG. 3) and is defined as the area between enlarged surfaces or bosses 30 (FIGS. 1 and 3) on bottom surface 20 of main board 12. Each of the enlarged surfaces 30 includes a plurality of tapped holes 32 in alignment therein. The lower or leg section 26 of main board 12 includes a pair of elongated members or runners 34 projecting from the bottom surface 20 for elevating the leg section 26 to enable one or more persons to insert a portion of their hands into an opening or slot 18 for grasping and lifting apparatus 10 or insert and attach a conventional strap for retaining a patient on apparatus 10. Main board 12 is made from a material such as molded polyethylene which encapsulates a polyurethane foam 36 (FIGS. 3 and 5) which provides rigidity to main board 12 and provides buoyancy to medical apparatus 10 if it ever becomes necessary to use medical apparatus 10 to rescue an injured person from water. The materials used to make main board 12 should be radiotransparent or x-ray penetrable to permit x-rays of the patient to be taken therethrough with no interference.

The x-ray cassette holder 14 is generally rectangular and U-shaped and comprises a mid section 38, a pair of spaced end sections 40 which protrude and extend from mid section 38, a top surface 42 (FIG. 7) and a bottom surface 44. Mid section 38 of x-ray cassette holder 14 is recessed as shown by reference numeral 46 (FIGS. 1 and 7) on its bottom surface 44. Each end section 40 includes a plurality of spaced, aligned, openings 50 therein.

The x-ray cassette holder 14 is assembled to the main board 12 by inserting screws 52 (one shown in FIG. 1) through each spaced, aligned opening 50 of x-ray cassette holder 14 and the screws 52 are screwed into an appropriate tapped hole 32 in the enlarged surfaces 30 in bottom surface 20 of main board 12.

FIG. 8 illustrates a patient lying on the immobilization board of the present invention (without conventional restraining straps) and having his torso area being examined by an x-ray machine 54. An x-ray cassette 56 is shown supported by the x-ray cassette holder 14.

The numerous openings or slots 18 near the outer perimeter of main or support board 12 provide handholds which allow for easy gripping and lifting of a patient placed upon the spinal board 10 and also provides slots from attaching an fixing conventional straps (not shown) for restraining the patient upon spinal board 12. Restraining straps adaptable for use with the spinal board of the present invention are readily available from numerous sources. These readily available straps include Items L95215, L95213, L95214, L95155, L95153, L95154, and L95464 sold by DynaMed, 6300 Yarrow Drive, Carlsbad, Calif. 92009 and described in its Winter/Spring Catalog for 1991, Catalog No. 1022. The conventional straps used in the mid or torso section 24 of main board 12 should be made of radiotransparent materials so to permit x-rays of the patient to be taken through the straps with no interference. Item L95464 described in the DynaMed catalog is illustrative of such a strap.

While the above description constitutes a preferred embodiment of the present invention, it will be appreciated that the invention is susceptible to modification, variation and change without departing from the proper scope and fair meaning of the accompanying claims.

I claim:

1. A portable apparatus for handling trauma victims during rescue, transfer, and diagnosis, including x-ray examination by an x-ray machine of the torso area of the trauma victim, comprising:

a substantially rectangular main board having a longitudinal axis and including a head section, a torso section, a leg section, a first pair of sides generally parallel to said longitudinal axis, a second pair of sides generally perpendicular to said longitudinal axis, a top surface, a bottom surface having a pair of spaced bosses protruding and extending therefrom, and defining a recessed area in said bottom surface between said bosses, said main board further including a plurality of spaced openings around the perimeter of said board;

a substantially rectangular, U-shaped x-ray cassette holder for supporting an x-ray cassette therein, said x-ray cassette holder including an intermediate section and a pair of spaced end sections which protrude and extend from said intermediate section; and means for rigidly securing said spaced end sections of said x-ray cassette holder to said bosses protruding from said bottom surface of said main board to provide a cavity defined by both said x-ray cassette holder and said recessed area in said lower surface, said cavity disposed for housing said x-ray cassette during an x-ray examination of the torso area of said trauma victim, said cavity including at least one side opening for receiving said cassette therein in normal relation to said longitudinal axis, said at least one side opening permitting simultaneous insertion of said x-ray cassette into said cavity and alignment of said x-ray cassette with a desired area of said victim and said x-ray machine.

2. The portable trauma victim handling apparatus of claim 1 including victim immoblization means secured to said main board and wherein said plurality of spaced openings around the perimeter of said main board provide means for gripping and lifting said apparatus and for securing said victim immobilization means.

3. The portable trauma victim handling apparatus of claim 2 wherein said leg section of said main board includes means on its said bottom surface for elevating said openings of said plurality of openings in said leg section from any surface upon which said apparatus might rest.

4. The portable trauma victim handling apparatus of claim 3 wherein said main board and said x-ray cassette holder is made of a molded polyethylene material.

5. The portable trauma victim handling apparatus of claim 4 wherein said main board incorporates means for providing buoyancy to said apparatus when rescuing a victim from water.

6. The portable trauma victim handling apparatus of claim 5 wherein said means for providing buoyancy to said apparatus comprises a polyurethane foam encapsulated within said main board.

7. The portable trauma victim handling apparatus of claim 6 wherein said spaced, end sections of said x-ray cassette holder is secured to said bosses on said bottom surface of said main board.

8. A portable apparatus for immobilizing a trauma victim during rescuing, transporting and subsequent x-ray examination by an x-ray machine of the torso area of the trauma victim, comprising:

a substantially rectangular main board including a longitudinal axis, a head section, an intermediate section, a leg section, a plurality of spaced, oblong, openings on the perimeter of said board, a top surface, and a bottom surface having a pair of spaced bosses protruding and extending therefrom, and defining a recessed area in said bottom surface between said bosses said bottom surface including at least one runner projecting downwardly from said leg section;

a substantially rectangular, U-shaped x-ray cassette holder for supporting an x-ray cassette therein, said x-ray cassette holder including an intermediate section and a pair of spaced end sections which protrude and extend from said intermediate section; and means for securing said spaced end sections of said U-shaped x-ray cassette holder to said bosses protruding and extending from said bottom surface of said main board adjacent the ends of said intermediate section of said main board to form a cavity defined by said x-ray cassette holder, said bosses, and said bottom surface of said main board for holding said x-ray cassette during x-ray examination of said trauma victim, said cavity including at least one side opening for receiving said cassette therein in normal relation to said longitudinal axis of said main board, said at least one side opening permitting simultaneous placing of said x-ray cassette into said cavity and alignment of said x-ray cassette with a desired area of said victim and said x-ray machine.

9. The portable trauma victim handling apparatus of claim 8 including victim immobilization means and wherein said spaced, oblong, openings around the perimeter of said main board provide means for gripping and lifting said apparatus and for securing said victim immobilization means.

10. The portable trauma victim handling apparatus of claim 9 wherein said main board and said x-ray cassette holder is made of a molded, x-ray penetrable, polyethylene material.

11. The portable trauma victim handling apparatus of claim 10 wherein said main board includes means therein for providing buoyancy to said apparatus when rescuing a victim from water.

12. The portable trauma victim handling apparatus of claim 11 wherein said means for providing buoyancy to said apparatus comprises a polyurethane foam encapsulated within said main board.

* * * * *